(12) United States Patent
Gala et al.

(10) Patent No.: US 6,943,251 B2
(45) Date of Patent: Sep. 13, 2005

(54) PREPARATION OF SALTS OF 4-[4-[(1R)-[4-(TRIFLUOROMETHYL)PHENYL]-2-METHOXYETHYL]-(3S)-METHYL-1-PIPERAZINYL]-4-METHYL-1-[(4,6-DIMETHYL-5-PYRIMIDINYL)CARBONYL]

(75) Inventors: Dinesh Gala, East Brunswick, NJ (US); Andrew J. Goodman, Annandale, NJ (US); Gary Lee, Oakland, CA (US); Hongbiao Liao, Edison, NJ (US); Martin L. Schwartz, Morris Plains, NJ (US); Suhan Tang, Edison, NJ (US); David Js Tsai, Warren, NJ (US); Wenxue Wu, Princeton Junction, NJ (US)

(73) Assignee: Schering Corporation, Kenilworth, NJ (US)

( * ) Notice: Subject to any disclaimer, the term of this patent is extended or adjusted under 35 U.S.C. 154(b) by 52 days.

(21) Appl. No.: 10/304,674

(22) Filed: Nov. 26, 2002

(65) Prior Publication Data

US 2003/0144510 A1 Jul. 31, 2003

Related U.S. Application Data

(60) Provisional application No. 60/373,916, filed on Apr. 19, 2002, and provisional application No. 60/334,331, filed on Nov. 29, 2001.

(51) Int. Cl.$^7$ ............................................. C07D 401/14
(52) U.S. Cl. ...................................................... 544/295
(58) Field of Search ........................................ 544/295

(56) References Cited

U.S. PATENT DOCUMENTS 6,391,814 B1 5/2002 Tsubokura et al. .......... 501/136

6,391,865 B1 * 5/2002 Baroudy et al. ............... 514/63

OTHER PUBLICATIONS

Bruzik, Karol, "Chapter 6: Conformation", Department of Medicinial Chemistry, University of Illinois at Chicago, [online] Nov. 10, 1998, [retrieved on Dec. 21, 2004]. Retrieved from the Internet, <http://tigger.uic.edu/~kbruzik/text/chapter6.html>.*

Clark Landis et al, "What does Chemistry have to do with AIDS?", Chemistry Department, University of Wisconsin [online] no date, [retrieved on Dec. 12, 2004]. Retd from the internet, <http://wwwchem.wisc.edu/~newtrad/CurrRef/AIDStopic/AIDStext/AIDSpp1.html.>.*

Paul M. Lahti, "Structural Analysis of Simple Amide", Department of Chemistry—U Mass. at Amherst [online] Aug. 11, 1998, [retrieved on Dec. 22, 2004]. Retrieved from the internet, <http://www..chem.umass.edu/~nermmw/amide.html>.*

Shriner, Ralph Lloyd, Fuson, Reynold C., and Curtin, David Y. "The Systematic Identification of Organic Compounds", New York: J. Wiley & Sons, 1956, p. 224.*

S. Berge et al., "Pharmaceutical Salts", *J. of Pharmaceutical Sciences*, 66(1): 1–19 (1977).

P. Gould, "Salt Selection for Basic Drugs", *International J. of Pharmaceutics*, 33: 201–217 (1986).

* cited by examiner

*Primary Examiner*—Thomas C. McKenzie
(74) *Attorney, Agent, or Firm*—Palaiyur S. Kalyanaraman

(57) ABSTRACT

In one embodiment, the present invention discloses a process to directly prepare an unequal ratio of rotamers of an acid salt from a basic compound, by creative choice of a solvent medium. The process is particularly useful in preparing specific rotamers of pharmaceutically useful salts in desired preponderance.

29 Claims, No Drawings

PREPARATION OF SALTS OF 4-[4-[(1R)-[4-(TRIFLUOROMETHYL) PHENYL]-2-METHOXYETHYL]-(3S)-METHYL-1-PIPERAZINYL]-4-METHYL-1-[(4, 6-DIMETHYL-5-PYRIMIDINYL)CARBONYL]

This application claims priority from U.S. provisional patent application Ser. No. 60/334,331 filed Nov. 29, 2001 and U.S. provisional patent application Ser. No. 60/373,916 filed Apr. 19, 2002.

FIELD OF THE INVENTION

This patent application generally discloses a novel process to prepare pharmaceutically useful salts. It specifically discloses a novel process to synthesize pharmaceutically useful salts of piperidine, 4-[4-[(1R)-[4-(trifluoromethyl) phenyl]-2-methoxyethyl]-(3S)-methyl-1-piperazinyl]-4-methyl-1-[(4,6-dimethyl-5-pyrimidinyl)carbonyl]. It further discloses a process to prepare pharmaceutical salts that are enriched in desired specific rotameric configurations.

BACKGROUND OF THE INVENTION

Piperidine, 4-[4-[(1R)-[4-(trifluoromethyl)phenyl]-2-methoxyethyl]-(3S)-methyl-1-piperazinyl]-4-methyl-1-[(4, 6-dimethyl-5-pyrimidinyl)carbonyl] (Formula I) is disclosed in pending U.S. patent application, Ser. No. 09/562, 814 filed on May 1, 2000, incorporated herein by reference.

I

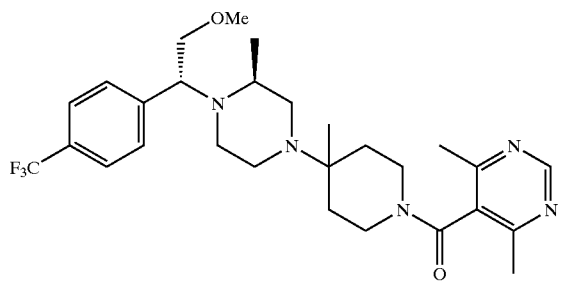

That patent application, Ser. No. 09/562,814, discloses several novel antagonists of the CCR5 receptor which are useful for the treatment of AIDS and related HIV infections, including the compound of Formula I. CCR-5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Generally, pharmaceutical compounds are used as their pharmaceutically acceptable salts. This is true of CCR5 receptor antagonists such as the compound of Formula I too, which makes the preparation of pharmaceutically acceptable salts of such compounds quite important.

The compound of Formula I has two chiral centers and the absolute configurations of the chiral centers are controlled by the chemical synthesis. However, the compound of Formula I exists as a mixture of rotational isomers or rotamers. There are two rotamers (diastereoisomers) resulting from restricted rotation about the amide bond marked in the figure in Scheme 1. The two rotamers may be denoted as isomers 1 and 2, in order of their elution from a HPLC column (Scheme 1):

Scheme 1

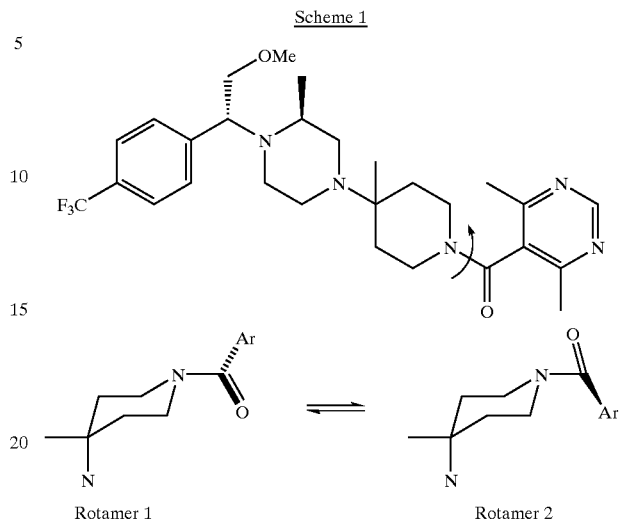

Rotamer 1        Rotamer 2

While general synthetic approaches for salts typically yield a 1:1 ratio of the rotamers 1 and 2, it would be preferable to find methods of synthesis that would yield rotamer populations that are enriched in certain rotamers preferentially.

SUMMARY OF THE INVENTION

In an embodiment, the present invention discloses a unique process for preparing a mixture of rotamers of a salt of a basic compound wherein said mixture comprises one or more rotamers of said salt in a higher (i.e., preferentially enriched) molar percent than their corresponding rotamers of said salt, with the process comprising reacting said basic compound with an acid in admixture with a solvent. It also teaches a method for preparing pharmaceutically useful salts. It specifically teaches a method for the formation of the salts, pharmaceutically useful or otherwise, of the compound of Formula I in high yields. It also teaches the direct, enriched preparation of specific, preferential rotamers of a salt of the compound of Formula I in high yields and in higher molar percent than other corresponding rotamers of the salt.

The term "high yields" refers to at least about 50% yield of the desired enriched product. Thus, unlike previously known processes which result in a 1:1 ratio of the salts of the rotamers 1 and 2, the present process offers a way to obtain the selective formation of unequal ratios of the salts of the desired rotamer directly. The term "higher molar percent" refers to selective preferred formation of a certain rotamer (or diastereoisomer) or rotamers over the other corresponding rotamer (or diastereoisomer) or rotamers by at least about a 55:45 ratio of molar percent. The formation of such differential ratio of rotamer (or diastereoisomer) directly in the present process is influenced by the unique choice of the solvent medium for the reaction between the particular acid and the basic compound. The term 'directly' means 'without the need for an additional step to separate the 50:50 rotamers obtained, for example, in the conventional process'. Thus, for example, if rotamer 2 is the desired one with high pharmaceutical activity, the present process makes it possible to obtain that rotamer directly instead of having to make an equimolar mixture of the rotamers 1 and 2 by previously known processes, followed by cumbersome separation of the mixture; such a separation may or may not yield the desired salt in decent yields and the process is also likely to be expensive.

Since the activity of pharmaceutical compositions may differ depending upon the type of salt they are comprised of, the present process affords a unique way to obtain desired specific salts with good pharmaceutical activity in highly enriched rotameric content. In the case of the compound of Formula I, the present process achieves such preferential formation of the isomers by creative selection of the acid (for salt formation) and solvent medium for the salt-forming reaction.

The inventive process to make differing ratio of the rotamers of the salts of the compound of Formula I has several advantages: it is economical, can be easily scaled-up, affords the desired, preferentially enriched rotamer ratio in high yields and is generically applicable.

DESCRIPTION OF THE INVENTION

In one embodiment, the present invention discloses a novel, easy-to-use process for preparing a pharmaceutical salt of a basic compound in high yields. In another embodiment, the present invention discloses a novel, easy-to-use process for preparing a pharmaceutical salt of a basic compound of Formula I in high yields. It also teaches the preferential preparation of specific rotamers of the salt of the compound of Formula I in high yields. In another embodiment, the present process, while described and illustrated herein as the preparation of specific desired rotamers of the compound of Formula I, is simple enough to be applicable generically to the preparation of pharmaceutically useful salts from a basic pharmaceutical composition. The present process comprises reacting the compound of Formula I (or a similar base) with an acid in admixture with a selected solvent medium in order to obtain differing ratios of rotamers as salts. The term "admixture" refers to physical contact of the ingredients as is known to those skilled in the art such as, for example, solution, suspension, emulsion, contact through a matrix such as, running through a column, and the like.

Thus, in another embodiment, the invention offers a novel, simple process to directly prepare desired salts of a basic compound in an unequal ratio of rotameric populations. In yet another embodiment, the present invention teaches the formation of pharmaceutically useful salts in high yields and selectivity of rotamer population.

In an illustrative embodiment, the present process offers a way to directly obtain at least about 55 mole percent of rotamer 2 and about 45 mole percent of rotamer 1 in the salt of the compound of Formula I. In many instances, it affords a way to obtain rotamer 2 and rotamer 1 in a molar percent ratio of 75:25 respectively. In fact, in several instances, it affords rotamer 2 in even greater than 90 molar percent. Specifically, the present process achieves such preferential formation of the desired rotamer of the salt of the compound of Formula I by creative selection of the acid (for salt formation) and solvent medium for the salt-forming reaction.

The process, while described and illustrated herein as the preparation of specific desired rotamers of the compound of Formula I, is simple enough to be applicable generically to the preparation of pharmaceutically useful salts from basic pharmaceutical compositions. By appropriate choice of the solvent medium, the reaction of the basic compound with an acid (from which the salt is to be derived) to form the salt selectively yields the desired rotameric compositions in enriched molar percent. Thus, in another embodiment, the invention offers a novel, simple process to directly prepare desired salts of basic compounds in an unequal ratio of rotamers. In yet another embodiment, the present invention teaches the formation of pharmaceutically useful salts in high yields and selectivity of rotamer population.

The following non-limiting list includes anions representing suitable acids which may be used to form salts in accordance with the present invention. The list of anions for useful salts includes, for example, acetate, benzenesulfonate, benzoate, bicarbonate, bromide, calcium edetate, camphorsulfonate, carbonate, chloride/dihydrochloride, citrate, N,N-di(dehydroabietyl) ethylenediamine, edetate, 1,2-ethanedisulfonate, ethanesulfonate, fumarate, glucoheptonate, gluconate, glutamate, p-glycollamidophenylarsonate, hexylresorcinate, hyclate, hydrobromide, hydrochloride, 2-hydroxyethanesulfonate, hydroxynaphthoate, iodide, lactate, lactobionate, lauryl sulfonate, malate, maleate, mandelate, methanesulfonate, methylbromide, methylnitrate, methylsulfate, mucate, nafate, napsylate, nitrate, pamoate, pantothenate, phosphate/diphosphate, polygalacturonate, salicyclate, sodium succinate, stearate, subacetate, succinate, sulfate, tosylate, tannate, tartarate/bitartarate, 8-chlorotheophyllinate, triethiodide, adipate, alginate, aminosalicyclate, anhydromethylenecitrate, arecoline, asparate, bisulfate, butylbromide, camphorate, digluconate, dihydrobromide, disuccinate, glycerophosphate, hemisulfate, hydrofluoride, hydroiodide, methylenebis(salicyclate), naphthalenedisulfonate, oxalate, pectinate, persulfate, phenylethylbarbiturate, picrate, propionate, thiocyanate, undecanoate, acetylaminoacetate, N-acetyl-L-asparaginate, N-acetylcystinate, adamantoate, adipoate, N-alkylsulfamates, anthraquinone-1,5-disulfonate, arabolactansulfate, argininate, aspartate, betaine, carnitine, 4-chloro-m-toluenesulfonate, decanoate, diacetyl sulfate, dibenzylethylenediamine, dimethylamine, diguaiacylphosphate, dioctylsulfosuccinate, pamoate, fructose-1,6-diphosphate, glucose phosphate, L-glutaminate, hydroxynaphthoate, lauryl sulfate, lysine, 2-naphthenesulfonate, octanonate, tannate and theobromine acetate. Additionally, acids which are generally considered suitable for the formation of pharmaceutically useful salts from basic pharmaceutical compounds are discussed, for example, by S. Berge et al, *Journal of Pharmaceutical Sciences* (1977) 66(1 ), 1–19; P. Gould, *International J. of Pharmaceutics* (1986) 33 201–217; Anderson et al, "The Practice of Medicinal Chemistry" (1996), Academic Press, New York; and in *The Orange Book* (Food & Drug Administration, Washington, D.C. on their website). These disclosures are incorporated herein by reference. Mono- and di- salts are included.

Generally, known processes to form salts by reaction of basic compounds with acids yield equal ratios of rotamers which need to be later separated in yet another step. The present process, which avoids such separation by preferentially enriching in certain rotamer populations during the salt formation reaction itself is superior.

The present process may be illustrated by the formation of the maleate salt of the compound of Formula I. The compound of Formula I, which is basic, may be dissolved in a suitable solvent. Suitable solvents include alcohol, ester, ketone, hydrocarbon or mixtures thereof. Non-limiting examples of such suitable solvents are ethyl acetate, isopropyl acetate, isopropyl alcohol, ethyl alcohol, acetone, hexane, toluene, heptane and the like, and mixtures thereof. Preferred solvents are ethyl acetate or isopropyl acetate. Maleic acid may be added to this either as a solid or as a solution in the same solvent. The acid is used generally in a 5:1 mole ratio, preferably in a 2:1 molar ratio and typically in a 1:1 molar ratio, with respect to the compound of Formula I. The total quantity of the solvent may generally be in about a 20:1 ratio, preferably about a 10:1 ratio and typically about a 6:1 ratio, with respect to the compound of Formula I. The mixture is stirred or intimately mixed otherwise, generally at about 25–90° C., preferably at about 50–90° C. and typically at about 60–80° C. for a duration of about 1–48 hours generally, about 1–36 hours preferably, and about 1–24 hours typically, and then kept at about the ambient conditions to allow the completion of salt formation, usually as crystals. Seeding may be done if necessary or desired. The salt may be isolated by filtration or such similar methods. The rotameric ratio may be determined by methods known to those skilled in the art such as, for example, HPLC, HMR and the like, as is well known to those skilled in the art. In an illustrative experiment involving the compound of Formula I, when ethyl acetate or isopropyl acetate was used as the solvent and maleic acid as the acid, a diastereomeric ratio of >2:98 (for the isomer 1 to the isomer 2) was found in the maleate salt formed from the reaction. Similar results were obtained for salts prepared with acids other than maleic acid too.

The salts prepared by the present invention exhibit desirable physical and chemical characteristics suitable for pharmaceutical uses. Non-limiting examples of such characteristics include physical stability, chemical stability, thermal stability, desirable hygroscopicity, solubility, fluidity and the like.

The following nonlimiting EXAMPLES and TABLE 1 are provided in order to further illustrate the present invention.

EXAMPLES

Unless otherwise stated, the following abbreviations have the stated meanings in the Examples and Table 1 below:
HPLC=High Performance Liquid Chromatography
M.pt:melting point
NMR=nuclear magnetic resonance spectroscopy
mL=milliliters
mmol=millimoles
g=grams
rt=room temperature (ambient)
THF=Tetrahydrofuran
TBME=Methyl t-butyl ether
ACN=Acetonitrile
EtOH=Ethanol
EtOAc=Ethyl acetate
iPrOAc=Isopropyl acetate

EXAMPLES

Example 1

Mono-benzenesulfonic Acid Salt of the Compound of Formula I

To 0.2 g (0.37 mmol) of the amine compound of Formula I dissolved in 1 mL ethyl acetate at 40° C. was added a solution of 0.06 g (0.38 mmol) benzene sulfonic acid in 1.5 mL EtOAc at 40° C. The solution was stirred 2 days and filtered. Solids were washed with 0.5 mL ethyl acetate and dried to give 40 mg of the mono-benzene sulfonate salt with 8.7:91.3 ratio of rotamers 1 to 2.

Example 2

Di-benzenesulfonic Acid Salt of the Compound of Formula I

To 0.3 g (0.55 mmol) of the amine compound of Formula I dissolved in 1 mL ethyl acetate at 40° C. was added a solution of 0.18 g (1.12 mmol) benzene sulfonic acid in 3 mL ethyl acetate at 40° C. The solution was stirred 2 days and filtered. Solids were washed with 0.5 mL ethyl acetate and dried to give 0.26 g of di-benzene sulfonate salt in 51.3% yield.

Example 3

Citric Acid Salt of the Compound of Formula I

To 6.14 g (9.18 mmol) of the amine compound of Formula I dissolved in 15 mL of acetone at 23° C. was added 1.77 g (9.17 mmol) of solid citric acid. The mixture was heated to 50° C. and allowed to cool to room temperature. The mixture was stirred for 23 hr and 15 mL of acetone was added. The solids were filtered, washed with 15 mL of acetone and dried to give 5.05 g of the citrate salt in 76% yield with 1:99 ratio of rotamers 1 to 2.

Example 4

Mono-hydrochloric Acid Salt of the Compound of Formula I

To 0.28 g (0.525 mmol) of the amine compound of Formula I dissolved in 1 mL MTBE at 23° C. was added 0.043 mL (0.52 mmol) 12 M HCl solution. The mixture was stirred for 10 days as the product slowly solidified. Two mL of TBME was added, the solids were filtered, washed with 2 mL THF and dried to give 0.25 g of the mono HCl salt in 85% yield.

Example 5

Di-hydrochloric Acid Salt of the Compound of Formula I

To 5.02 g (9.22 mmol) of the amine compound of Formula I dissolved in 22.5 mL of 2:1 THF: toluene at 23° C. was added 1.55 ml (18.7 mmol) 12 M HCl solution. The mixture was stirred for 23 hr and filtered. The solids were washed with 15 mL THF and dried to give 5.2 g of the di-HCl salt in 92% yield with 1:99 ratio of rotamers 1 to 2.

Example 6

Fumaric Acid Salt of the Compound of Formula I

To 0.5 g (0.92 mmol) of the amine compound of Formula I dissolved in 0.5 mL toluene and 2.5 mL acetone at room temperature was added 0.1145 g (0.987 mmol) fumaric acid and 2.5 mL acetone. The solution was stirred for 2 days, cooled to 0° C. and filtered to give 0.29 g of the mono-fumarate salt.

Example 7

Di-phosphoric Acid Salt of the Compound of Formula I

To 0.30 g (0.55 mmol) of the amine compound of Formula I dissolved in 1.5 mL isopropyl alcohol was added 75 μL (1.10 mmol) 85% phosphoric acid at 40° C. The solution was stirred for 2 days, filtered and dried to give 0.35 g of the diphosphate salt in 85.2% yield.

Example 8

Mono-p-toluene Sulfonic Acid Salt of the Compound of Formula I

To 0.23 g (0.44 mmol) of the amine compound of Formula I dissolved in 1 mL isopropyl acetate at 40° C. was added a solution of 0.0845 g (0.24 mmol) p-toluene sulfonic acid monohydrate in 1.5 mL isopropyl acetate at 40° C. The solution was stirred 2 days and filtered. Solids were washed with 0.5 mL isopropyl acetate and dried to give 0.17 g of mono-PTSA salt in 54.6% yield with 7.7:92.3 ratio of rotamers 1 to 2.

Example 9

Di-p-toluene Sulfonic Acid Salt of the Compound of Formula I

To 0.30 g (0.44 mmol) of the amine compound of Formula I dissolved in 1 mL acetone at 40° C. was added a solution of 0.1686 g (0.89 mmol) p-toluene sulfonic acid monohydrate in 3 mL acetone at 40° C. The solution was stirred 2 days and filtered. Solids were washed with 1.5 mL acetone and dried to give 0.2 g of the di-PTSA salt.

The following Examples illustrate the preparation of the maleic acid salt of the compound of Formula I from different solvents:

Example 10a

From Isopropanol

The amine compound of Formula I (3.0 g, 93.6% pure) and maleic acid (0.65 g) were mixed and dissolved in isopropanol (12 mL). The mixture was stirred at room temperature for about 1 h resulting in a cloudy solution. Crystalline seeds were added and the resulting slurry was stirred at room temperature for about 21 h. The product was filtered and dried overnight at 55° C. under vacuum to give a white solid (3.0 g, 88% yield). Ratio of rotamers 1 to 2: 1.1:98.9.

Example 10b

From Ethanol/Toluene Mixture

The amine compound of Formula I (10 g) in ethyl acetate (about 35 mL) was mixed with a solution of maleic acid (2.17 g) in methanol (10 mL) at room temperature. The mixture was concentrated under vacuum and the residue was redissolved in ethanol (10 mL). Toluene (125 mL) was added slowly at 60° C. to give a milky solution. The mixture was cooled to room temperature over 2 h and seeded. The mixture was stirred at room temperature for about 2.5 days. The product was filtered and dried for 18 h at 45° C. under vacuum to give a white solid (8.66 g, 71% yield). Ratio of rotamers 1 to 2: 1.8:98.2.

Example 10c

From Ethanol/Ethyl Acetate Mixture

The amine compound of Formula I (10 g) in ethyl acetate (35 mL) was mixed with a solution of maleic acid (2.18 g) in ethanol (10 mL) at room temperature. Crystalline seeds were added and the mixture was stirred at room temperature for 22 h. The slurry was cooled gradually to −10° C. and stirred at that temperature for 4 h. The product was filtered, washed with ethyl acetate (10 mL), and dried overnight at 64° C. under vacuum to give the desired salt as a white solid. Ratio of rotamer 1 to 2: 2.3:97.7.

Example 10d

From Isopropanol/Ethyl Acetate

The amine compound of Formula I (10 g) in ethyl acetate (40 mL) was mixed with a solution of maleic acid (2.2 g) in isopropanol (20 mL) at 55° C. The cloudy mixture was seeded, cooled slowly to 40° C., and stirred at 40° C. overnight. The resulting slurry was cooled gradually to room temperature and stirred overnight. The product was filtered, washed with 2:1 ethyl acetate/isopropanol (30 mL), and dried overnight at 55° C. under vacuum to give the desired salt as a white solid. Ratio of rotamers 1 to 2: 0.9:99.1.

Example 10e

From Ethyl Acetate

The amine compound of Formula I (26 g) in ethyl acetate (26 mL) was mixed with a solution of maleic acid (5.7 g) in Ethyl Acetate (74 mL) at 60° C. The solution was seeded at 60° C. and stirred at 60° C. overnight. The resulting slurry was cooled gradually to room temperature and to 0° C. for 2 hours. The product was filtered, and dried overnight at 25° C. under vacuum to give a white solid (27.6 g, 87% yield). Ratio of rotamers 1 to 2: 1.8:98.2.

Example 10f

From Ethyl Acetate/Heptane

The amine compound of Formula I (20 g) in ethyl acetate (20 mL) was mixed with a solution of maleic acid (4.4 g) in Ethyl Acetate (60 mL) at 65° C. The solution was seeded at 65° C. and stirred at 65° C. for 1 hours. Then 20 mL of Heptane was added to the slurry at 65° C. After stirring at 65° C. overnight, the slurry was cooled gradually to room temperature and to 0° C. for 2 hours. The product was filtered, and dried overnight at 25° C. under vacuum to give a white solid (22.3 g, 92% yield). Ratio of rotamers 1 to 2: 1.9:98.1.

Example 10g

From Isopropyl Acetate

Maleic acid (4.4 g) was dissolved in 100 mL of Isopropyl acetate at 75° C. The solution of the amine compound of Formula I (20 g) in Isopropyl acetate (20 mL) was added to the maleic acid solution at 75° C. After stirring at 75° C. overnight, the resulting slurry was cooled gradually to room temperature and to 0° C. for 2 hours. The product was filtered, and dried overnight at 25° C. under vacuum to give a white solid (22.1 g, 91% yield). M.pt. 183.5° C. Ratio of rotamers 1 to 2: 1.8:98.2.

TABLE 1

| Salt | Solvent (diastereomeric ratio 1 to 2 in solids) Yield % | | | | |
|---|---|---|---|---|---|
| 1. Mono-Benzene sulfonate | Ethyl Acetate (8.7:91.3) | | | | |
| 2. Di-Benzene sulfonate | Ethyl Acetate 51% yield | TBME 94% yield | | | |
| 3. (1S)-(+)-Camphorsulfonate | THF/TBME (50:50) | | | | |
| 4. Citrate | Acetone (1:99) | | | | |
| 5. Mono-hydrochloride | TBME 85% yield | | | | |
| 6. Di-hydrochloride | THF/Toluene (1:99) | | | | |
| 7. Fumarate | Acetone 66% yield | Acetonitrile 76% yield | iPrOAc 51% yield | Acetone/ Toluene | |
| 8. Di-Phosphate | Acetone 69% yield | Ethyl Acetate 57% yield | Isopropyl alcohol 85% yield | | |
| 9. Mono-Tosylate | Ethyl Acetate | iPrOAc (7.7:92.3) | | | |
| 10 Di-Tosylate | Acetone 50% yield | Ethyl Acetate | IPrOAc or Toluene | Isopropyl alcohol | TBME 99.5% yield |
| 11 Maleate | Ethyl Acetate (1.8:98.2) Ethyl Acetate/ Heptane (1.9:98.1) | iPrOAc (1.8:98.2) | EtOH/Ethyl Acetate (2.3:97.7) EtOH/ toluene (1.8:98.2) | Isopropyl alcohol (1.1:98.9) Isopropyl alcohol/ EtOAc (0.9:99.1) | |

While the EXAMPLES and TABLE 1 are described herein as the preparation of the diastereomeric isomer of the salts of the compound of Formula I, it will be apparent to those skilled in the art that many modifications, variations and alterations to the present disclosure, both to materials, methods and reaction conditions, may be practiced. All such modifications, variations and alterations are intended to be within the spirit and scope of the present invention.

What is claimed is:

1. A mono-benzene sulfonate salt of a basic compound, wherein said basic compound has the formula:

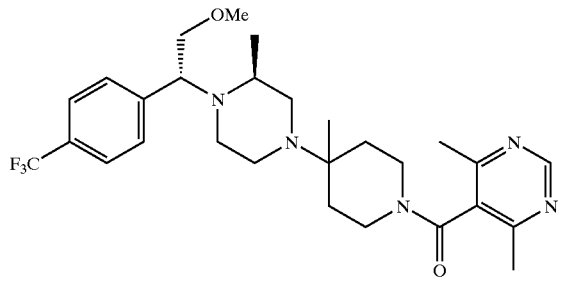

wherein said salt is prepared by a process comprising reacting said basic compound with benzenesulfonic acid in admixture with a solvent, wherein said acid is used in a molar ratio of about 5:1 with respect to said basic compound and said solvent is used in a molar ratio of about 20:1 with respect to said basic compound.

2. A mono-tosylate salt of a basic compound, wherein said basic compound has the formula:

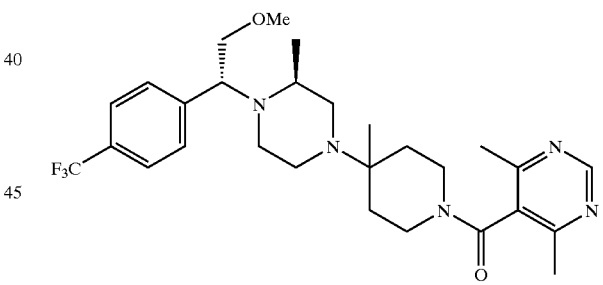

wherein said salt is prepared by a process comprising reacting said basic compound with toluene sulfonic acid in admixture with a solvent, wherein said acid is used in a molar ratio of about 5:1 with respect to said basic compound and said solvent is used in a molar ratio of about 20:1 with respect to said basic compound.

3. A process for preparing a mixture of rotamers of a salt of a basic compound wherein said mixture comprises one or more rotamers of said salt in a higher molar percent than their corresponding rotamers of said salt, said process comprising reacting said basic compound with an acid in admixture with a solvent, wherein said basic compound has the structure of Formula I:

Formula I

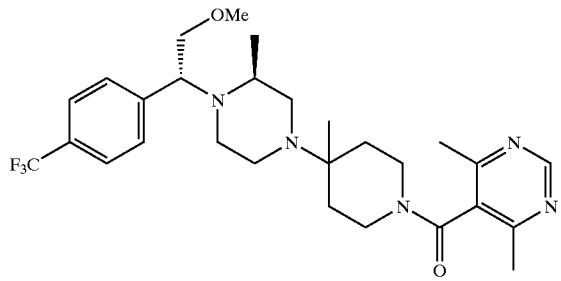

wherein said acid is used in a molar ratio of about 5:1 with respect to said basic compound and said solvent is used in a molar ratio of about 20:1 with respect to said basic compound.

4. The process of claim 3, wherein said higher molar percent refers to the ratio of the salt of rotamer 1 to the salt of rotamer 2 of said compound of Formula I.

5. The process of claim 3, wherein said higher molar percent refers to the ratio of the salt of rotamer 2 to the salt of rotamer 1 of said compound of Formula I.

6. The process of claim 3, wherein said salt is selected from the group consisting of benzenesulfonate, citrate, camphorsulfonate, maleate, fumarate. phosphorate; p-toluenesulfonate, (D)-camphorate, and hydrochloride.

7. The process of claim 6, wherein said salt is maleate.

8. The process of claim 3, wherein said solvent is an alcohol, ester, ketone, hydrocarbon or mixtures thereof.

9. The process of claim 8, wherein said alcohol is selected from the group consisting of ethyl alcohol, isopropyl alcohol and mixtures thereof.

10. The process of claim 9, wherein said alcohol is isopropyl alcohol.

11. The process of claim 8, wherein said hydrocarbon is selected from the group consisting of toluene, hexane, heptane and mixtures thereof.

12. The process of claim 8, wherein said ester is selected from the group consisting of ethyl acetate, isopropyl acetate and mixtures thereof.

13. The process of claim 7, wherein said maleate is formed at a temperature range of about ambient temperature to about 90° C.

14. The process of claim 13, wherein said solvent is ethyl acetate.

15. The process of claim 13, wherein said solvent is isopropyl acetate.

16. The process of claim 13, wherein said solvent is isopropyl alcohol.

17. The process of claim 13, wherein said solvent is a mixture of ethyl alcohol and toluene.

18. The process of claim 13, wherein said solvent is a mixture of ethyl acetate and heptane.

19. The process of claim 7, wherein said maleate is formed at about the ambient temperature over about 21 hours.

20. The process of claim 6, wherein said salt is a citrate.

21. The process of claim 20, wherein said solvent is acetone and the reaction is performed at about 50° C. for about 23 hours.

22. The process of claim 3, wherein said molar percent is about 55:45 of said one or more rotamers of the salt to said other corresponding rotamers of the salt.

23. The process of claim 22, wherein said molar percent is about 75:25 of said one or more rotamers of the salt to said other corresponding rotamers of the salt.

24. The process of claim 23, wherein said molar percent is at least about 90:10 of said one or more rotamers of the salt to said other corresponding rotamers of the salt.

25. A process for preparing a mixture of rotamer 1 and rotamer 2 of the maleate salt of the compound of Formula I Formula I

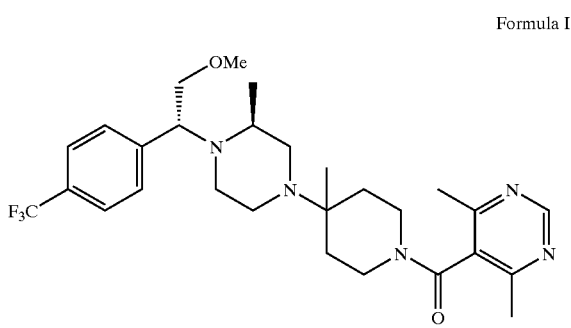

wherein the molar percent of said rotamer 2 to the molar percent of said rotamer 1 in said mixture is in at least about a 55:45 ratio, said process comprising;
(a) preparing a first intimate mixture of said compound of Formula I in a solvent;
(b) maintaining said first intimate mixture at about ambient temperature to about 90° C.
(c) preparing a second intimate mixture of maleic acid in the same solvent stated in step (a);
(d) combining said first intimate mixture and said second intimate mixture to prepare a combined intimate mixture and maintaining the combined intimate mixture at about ambient temperature to about 90° C. for about 1–24 hours to induce formation of the maleate salt; and
(e) isolating the salt,
wherein said solvent is an alcohol, ketone, ester, hydrocarbon or mixtures thereof.

26. The process of claim 25, wherein said solvent is an alcohol.

27. The process of claim 25, wherein said ester is isopropyl acetate or ethyl acetate.

28. The process of claim 25, wherein said ratio is about 75:25 for the molar percent of rotamer 2 to the molar percent of rotamer 1.

29. The process of claim 25, wherein said ratio is at least about 90:10 for the molar percent of rotamer 2 to the molar percent of rotamer 1.

* * * * *

UNITED STATES PATENT AND TRADEMARK OFFICE
CERTIFICATE OF CORRECTION

PATENT NO. : 6,943,251 B2  Page 1 of 1
APPLICATION NO. : 10/304674
DATED : September 13, 2005
INVENTOR(S) : Gala et al.

It is certified that error appears in the above-identified patent and that said Letters Patent is hereby corrected as shown below:

On the Title Page, Item (54):
Please insert "PIPERIDINE," between -- SALTS OF -- and
-- 4-4[4-[(1R)-4-TRIFLUOROMETHYL)--

Signed and Sealed this

Seventeenth Day of October, 2006

JON W. DUDAS
*Director of the United States Patent and Trademark Office*